United States Patent
Devassine et al.

(10) Patent No.: US 11,478,417 B2
(45) Date of Patent: Oct. 25, 2022

(54) FRAGRANCE PRODUCT

(71) Applicant: AKI, Inc., Chattanooga, TN (US)

(72) Inventors: Mickael Devassine, Chattanooga, TN (US); Hrazhyna Devassine, Ooltewah, TN (US)

(73) Assignee: AKI, Inc., Chattanooga, TN (US)

( * ) Notice: Subject to any disclaimer, the term of this patent is extended or adjusted under 35 U.S.C. 154(b) by 0 days.

(21) Appl. No.: 16/839,536

(22) Filed: Apr. 3, 2020

(65) Prior Publication Data

US 2020/0315946 A1    Oct. 8, 2020

Related U.S. Application Data

(60) Provisional application No. 62/829,788, filed on Apr. 5, 2019.

(51) Int. Cl.

| | | |
|---|---|---|
| *A61K 8/891* | (2006.01) | |
| *A61K 8/04* | (2006.01) | |
| *A61K 8/37* | (2006.01) | |
| *A61K 8/86* | (2006.01) | |
| *A61Q 19/00* | (2006.01) | |
| *A61Q 13/00* | (2006.01) | |

(52) U.S. Cl.
CPC ............. *A61K 8/891* (2013.01); *A61K 8/04* (2013.01); *A61K 8/042* (2013.01); *A61K 8/37* (2013.01); *A61K 8/375* (2013.01); *A61K 8/86* (2013.01); *A61Q 13/00* (2013.01); *A61Q 19/007* (2013.01); *A61K 2800/31* (2013.01)

(58) Field of Classification Search
CPC ........ A61K 8/04; A61K 2800/30; A61K 8/37; A61K 2800/594; A61K 8/042; A61K 8/891; A61K 8/375; A61K 8/86; A61K 2800/31; A61Q 19/007; A61Q 13/00
See application file for complete search history.

(56) References Cited

U.S. PATENT DOCUMENTS

| | | | | |
|---|---|---|---|---|
| 5,110,809 | A * | 5/1992 | Wang | ................... A61K 9/0014 |
| | | | | 514/171 |
| 6,248,339 | B1 | 6/2001 | Knitowski | |
| 9,526,738 | B2 | 12/2016 | Stasko | |
| 2008/0206172 | A1 | 8/2008 | Mohammadi | |
| 2009/0081316 | A1* | 3/2009 | Wahl | ...................... A61K 8/891 |
| | | | | 424/657 |
| 2009/0214458 | A1 | 8/2009 | Brun | |
| 2010/0184714 | A1* | 7/2010 | Raul | ....................... A61P 17/06 |
| | | | | 514/29 |
| 2013/0344121 | A1 | 12/2013 | Kim | |
| 2016/0250137 | A1 | 9/2016 | Noor | |
| 2018/0015022 | A1* | 1/2018 | Efthimios | ................ A61K 8/25 |

FOREIGN PATENT DOCUMENTS

| | | |
|---|---|---|
| DE | 102013223789 A1 | 4/2014 |
| WO | 2012098116 A1 | 7/2012 |
| WO | 2019096954 A1 | 5/2019 |

OTHER PUBLICATIONS

Momentive, "Velvesil DM silicone", download from http://docplayer.net/38875861-Velvesil-dm-silicone.html on Sep. 26, 2021. (Year: 2021).*
Written Opinion of the International Searching Authority, PCT/US2021/026921, dated Jul. 8, 2021.

* cited by examiner

*Primary Examiner* — Jianfeng Song
(74) *Attorney, Agent, or Firm* — Rivkin Radler LLP

(57) ABSTRACT

An anhydrous and alcohol-free slow fragrance diffusive composition (lotion, gel or cream) with longer lasting properties than hydroalcoholic formula fragrance product that contains 50 to 75 percent by weight dimethicone crosspolymer gel, 0.01 to 30 percent by weight fragrance oil and 5 to 40 percent by weight volatile linear silicone fluid. Emollients may be added to moisturize the skin, improve the fragrance rendition and/or increase the miscibility of the fragrance oil in the composition when a high level of dimethicone is used (in case of a lotion for example). Moreover, a preservative and some pigments can be added to the formula to preserve the fragrant product from bacteria contamination and to improve the aesthetics respectively.

13 Claims, No Drawings

FRAGRANCE PRODUCT

CROSS-REFERENCE TO RELATED APPLICATION

The present application claims priority to U.S. Provisional Patent Application Ser. No. 62/829,788 filed Apr. 5, 2019 and entitled "ANHYDROUS SILKY FRAGRANCE PRODUCT" which is hereby incorporated herein by reference in entirety for all purposes.

FIELD OF THE INVENTION

The present invention relates to a slow release fragrance diffusive product which improves fragrance lift without alcohol flash. The presence of silicone gel allows a silky application of the fragrance and the absence of alcohol avoids the drying of the skin. The crosspolymer creates a barrier to let the fragrance adhere to the skin and help to maintain moisture of the skin. The volatile linear silicone improves fragrance lift from the skin and avoids an oily feel on the skin.

BACKGROUND OF THE INVENTION

Ethanol is widely used as a solvent for fine fragrances. The safety of topical applications of ethanol is still a matter of debate, and there appears to be scientific evidence pointing in both directions. On the one hand, researchers concluded that the range of damage caused to the skin by the alcohol cannot and should not be ignored, although the deleterious effects of ethanol exposure on the skin may pale into insignificance compared to its effects on the liver, central nervous system, and other body systems after ingestion. On the other hand, scientific studies attributed ethanol for topical uses as safe per se. However, there appears to be at least some evidence, including epidemiological data, about mouthwash use, and data from animal experiments showing that ethanol on the skin or inside the oral cavity may cause harm if used chronically. Evaluation, according to EU cosmetics legislation and other acts about chemical safety, should consider the chronic toxic and carcinogenic potential of ethanol. In Lachenmeier's article (Dirk W. Lachenmeier, Safety evaluation of topical applications of ethanol on the skin and inside the oral cavity, J. Occup. Med. Toxicol., 2008; 3: 26), the safety of topical uses of ethanol was evaluated by a critical review of the scientific literature. The author mentioned that ethanol abuse has been associated with the development of several skin disorders such as psoriasis, discoid eczema and superficial infections. Chronic alcohol abuse was also a predisposing factor for necrotizing wound infections, delayed wound healing and cellulitis.

Therefore, there is a need for improved fine fragrance solution compositions that have a fragrance lift from the skin while avoiding the negative effects of ethanol (drying of skin, skin diseases . . . ) but have at the same time a silky texture, maintain the desired clarity and are aesthetically pleasing to the consumer.

U.S. Pat. No. 6,248,339 to Knitowski, et al., assigned to Intimate Beauty Corporation, discloses a fragrant body lotion or cream, which utilizes a cyclomethicone/dimethicone crosspolymer gel which contains a volatile cyclomethicone and a fragrance oil. Volatile cyclomethicone are becoming more and more restricted, particularly in Europe, because some of them, such as cyclotetrasiloxane (D4), are considered toxic to the human reproductive system. At the beginning of 2017 the European Commission (EC) proposed to ban D4 and D5 (cyclopentasiloxane) in rinse-off cosmetic products, with 0.1% or more of either substance. This ban, when officially published, is going to cover products such as shampoos, conditioners, shower gels . . . . The European Chemicals Agency (ECHA) plans to go even further and to extend the restriction to leave on personal care products intended to remain on the skin.

U.S. Pat. No. 2008/0206172 to Mohammadi et al., assigned to The Estee Lauder Cos, relates clear sunscreen gels, which contain chemical ultra-violet light absorber, one solvent such as dimethicone and a diphenyl silicone elastomer gellant.

U.S. Pat. No. 9,526,738 relates to non-aqueous topical gels for the treatment of wounds and other skin ailments. These gels comprise diazeniumdiolate-functionalized polysiloxane macromolecules at a concentration in range of 0.1 to 20 weight %, cyclomethicone at a concentration in a range of 5 to 30 weight % and crosslinked polydimethylsiloxane at a concentration in a range of 65 to 85 weight %.

DESCRIPTION OF THE PREFERRED EMBODIMENTS

The slow-release fragrance diffusive product of the invention contains about 50 to 75 percent by weight anhydrous dimethicone crosspolymer gel, 0.01 to 30 percent in weight fragrance oil and 5 to 40 percent by weight volatile linear silicone fluid. The formula doesn't contain alcohol or water. The viscosity of the gel is adjusted by the ratio volatile linear silicone fluid/dimethicone crosspolymer gel. Emollients such as isononyl isononanoate, triethyl citrate, PPG-20 Methyl Glucose Ether and/or caprylic/capric triglycerides may be added to the formula to increase the miscibility of the fragrance, improve the fragrance rendition and/or to keep the skin moist and flexible, helping to prevent cracks.

The fragrance product contains dimethicone crosspolymer gel. That gel is composed of 7-20% dimethicone crosspolymer in linear silicone fluid. The gel is preferentially composed of 8-12% dimethicone crosspolymer in linear silicone fluid. The preferred crosspolymers are dimethicone or vinyl dimethicone crosspolymer in dimethicone fluid. Examples of silicone crosspolymer include acrylates/bis-hydroxypropyl dimethicone crosspolymer, behenyl dimethicone/bis-vinyldimethicone crosspolymer, bis-phenylisopropyl phenylisopropyl dimethicone/vinyl dimethicone crosspolymer, bis-vinyldimethicone/bis-isobutyl PPG-20 crosspolymer, bis-vinyldimethicone crosspolymer, bis-vinyldimethicone/PEG-10 dimethicone crosspolymer, bis-vinyldimethicone/PPG-20 crosspolymer, butyldimethicone methacrylate/methyl methacrylate crosspolymer, C30-45 alkyl cetearyl dimethicone crosspolymer, C4-24 alkyl dimethicone/divinyldimethicone crosspolymer, C30-45 alkyl dimethicone/polycyclohexene oxide crosspolymer, cetearyl dimethicone crosspolymer, cetearyl dimethicone/vinyl dimethicone crosspolymer, cetyl dimethicone/bis-vinyldimethicone crosspolymer, cetyl hexacosyl dimethicone/bis-vinyldimethicone crosspolymer, crotonic acid/vinyl C8-12 isoalkyl esters/VA/bis-vinyldimethicone crosspolymer, dimethicone/bis-isobutyl PPG-20 crosspolymer, dimethicone/bis-vinyldimethicone/silsesquioxane crosspolymer, dimethicone crosspolymer, dimethicone crosspolymer-3, dimethicone/divinyldimethicone/silsesquioxane crosspolymer, dimethicone/lauryl dimethicone/bis-vinyldimethicone crosspolymer, dimethicone/PEG-10 crosspolymer, dimethicone/PEG-10/15 crosspolymer, dimethicone/PEG-15 crosspolymer, dimethicone/phenyl vinyl dimethicone crosspolymer, dimethicone/polyglycerin-3 crosspolymer, dimethicone/PPG-20 crosspolymer, dimethicone/titanate crosspolymer, dimethicone/vinyl dimethicone crosspolymer, dimethicone/vinyltrimethylsiloxysilicate crosspolymer, diphenyl dimethicone crosspolymer, diphenyl dimethicone/vinyl diphenyl dimethicone/silsesquioxane crosspolymer, divinyldimethicone/dimethicone crosspolymer, hydroxypropyl dimethicone/polysorbate 20 crosspolymer, isopropyl titanium triisostearate/triethoxysilylethyl polydimethylsiloxyethyl dimethicone crosspolymer, lauryl dimethicone PEG-15 crosspolymer, lauryl dimethicone/polyglycerin-3 crosspolymer, lauryl polydimethylsiloxyethyl dimethicone/bis-vinyldimethicone crosspolymer, PEG-10 dimethicone crosspolymer, PEG-12 dimethicone crosspolymer, PEG-8 dimethicone/polysorbate 20 crosspolymer, PEG-12 dimethicone/bis-isobutyl PPG-20 crosspolymer, PEG-12 dimethicone/PPG-20 crosspolymer, PEG-10 dimethicone/vinyl dimethicone crosspolymer, PEG-10/lauryl dimethicone crosspolymer, PEG-15/lauryl dimethicone crosspolymer, PEG-15/lauryl polydimethylsiloxyethyl dimethicone crosspolymer, perfluorononyl dimethicone/methicone/amodimethicone crosspolymer, polydimethylsiloxyethyl dimethicone/bis-vinyldimethicone crosspolymer, polyglyceryl-3/lauryl polydimethylsiloxyethyl dimethicone crosspolymer, silicone quaternium-16/glycidoxy dimethicone crosspolymer, styrene/acrylates/dimethicone acrylate crosspolymer, trifluoropropyl dimethicone/PEG-10 crosspolymer, trifluoropropyl dimethicone/trifluoropropyl divinyldimethicone crosspolymer, trifluoropropyl dimethicone/vinyl trifluoropropyl dimethicone/silsesquioxane crosspolymer, trimethylsiloxysilicate/dimethicone crosspolymer, vinyl dimethicone crosspolymer, vinyl dimethicone/lauryl/behenyl dimethicone crosspolymer, vinyl dimethicone/lauryl dimethicone crosspolymer, vinyl dimethicone/methicone silsesquioxane crosspolymer, vinyldimethyl/trimethylsiloxysilicate/dimethicone crosspolymer and vinyldimethyl/trimethylsiloxysilicate stearyl dimethicone crosspolymer. The crosspolymer is pre-mixed in the same volatile linear silicone that is used in the invention.

The fragrance which can be used in the present invention, either in the form of a single compound, or in the form of a mixture of fragrance ingredients forming a perfuming composition, are all ingredients commonly used in perfumery. These ingredients shall not be described in greater detail here, as their description cannot be exhaustive, and the skilled person is able to choose them by using his general knowledge and as a function of the desired olfactory effect. These perfuming ingredients belong to a variety of chemical classes, as varied as acid, alcohols, aldehydes, ketones, esters, ethers, acetates, nitriles, terpenic hydrocarbons, heterocyclic nitrogen- or sulfur-containing compounds as well as essential oils of natural or synthetic origin. Many of these ingredients are furthermore described in fragrance books. The nature of the perfuming ingredients is not an essential parameter of the invention, and the latter shall be chosen as a function of the fragrance or odorous effect that it is desired. The fragrance is preferentially non-polar to keep the clarity of the product of the invention.

The volatile linear silicone is a polydimethylsiloxane or dimethicone which has a relatively low average molecular weight, a relatively low viscosity and a significant vapor pressure at 25 degree C. (i.e. one gram of fluid placed on No. 1 filter paper leaves substantially no visible residue after thirty minutes at room temperature). It also typically has a boiling point under 250 degree C. The volatile linear silicone (or volatile dimethicone) is represented by the formula in FORMULA 1 (CH sub.3)sub.3 SiO(Si(CH sub.3)sub.2 O).sub.n Si(CH sub.3)sub.3 in which n is an integer of about 0 to about 6, preferably about 1 to about 4.

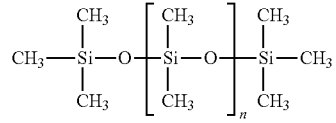

FORMULA 1

One of the methyl groups of the foregoing formula may be replaced with an alkyl group (e.g. of 2 to 10 carbon atoms) to provide an alkylmethylsiloxane. Such material includes, for example, Dowsil FZ-3196 Fluid (caprylyl Methicone from Dow Corning), which is 1,1,1,3,5,5,5-Heptamethyl-3-octyl-trisiloxane (viscosity=2.9 cSt). While a pure silicone polymer may be utilized, generally the volatile linear silicone is a mixture of silicone polymers of the above formula. The volatile linear silicone will have a viscosity of less than about 5 cSt (or less than about 5 cP), preferably between about 0.6 and 3.0 cSt, more preferably between 1.0 and 2.0 cSt. (For silicones with a specific gravity at 25 degree C. in the 0.75 to 0.92 range, the foregoing viscosity ranges convert to about 0.5 to 2.8 cP, preferably about 0.8 to 1.8 cP) Suitable volatile linear silicones include Xiameter PMX-200 Silicone Fluid 0.65 cSt or ICM SF-0.65 or DM-Fluid-0.65 cs (hexamethyldisiloxane), Xiameter PMX-200 Silicone Fluid 1.0 cs or ICM SF-1.0 or DM-Fluid-1 cs (octamethyltrisiloxane), Xiameter PMX-200 Silicone Fluid 1.5 cSt or ICM SF-1.5 or DM-Fluid-1.5 cs (decamethyltetrasiloxane), Xiameter PMX-200 Silicone Fluid 2.0 cSt or ICM SF-2.0 or DM-Fluid-2 cs (dodecamethylpentasiloxane). Xiameter PMX-200 Silicone Fluids, ICM SF and DM-Fluid, all available from Dow Corning, CHT and ShinEtsu, respectively. ICM SF-1.5 which has a viscosity of about 1.6 cSt and an average molecular weight of about 310 (i.e. n is about 2 in the above formula) is preferred.

An emollient may be added to the formulation because it can provide a moisturizing effect to the composition by forming a barrier layer on the skin to minimize water loss. The emollients include esters (most common), fatty alcohols, fatty acids, ethers, silicones, and hydrocarbons. Preferably, the emollient is a liquid at room temperature (25° C.). Waxes and oils that are solid at room temperature are generally not preferred.

The emollient is preferably a linear or branched ester. Esters are resulted from the reaction of polyols or alcohols with acids, with the formula Ri—COO—R, R and $R_1$ each having a carbon chain length of up to 10 carbon atoms, and preferably having a carbon chain length of from three carbon atoms to 10 carbon atoms. R and Ri may have the same carbon chain length or may have different carbon chain lengths. R may be from an alkyl moiety or a polyol moiety. Suitable alkyl moieties may include, for example, ethylhexyl, isononyl, isodecyl, isopropyl, and caprylyl. Suitable polyol moieties may include, for example, glycerol, neopentyl glycol, butylene glycol, pentylene glycol, sorbitol, hexylene glycol, and caprylyl glycol. Ri can be from an acyl moiety of a mono- or di-carboxy fatty acid. Suitable monoacyl moieties may include heptanoyl (heptanoic acid), caprioyl (caprylic acid), isooctanoyl (isooctanoic acid), isononanoyl (isononanoic acid) or neopentanoyl (neopentanoic acid). Suitable acyl moieties for di-carboxy acids may include adipoyl (adipic acid) or sebacoyl (sebacic acid). A preferred emollient is isononyl isononanoate. Other suitable emollients include isooctyl isooctanoate, diisopropyl adipate, glycerin heptanoate, ethylhexyl caprylate, diisopropyl sebacate, neopentylglycol diheptanoate, and isodecyl neopentanoate.

Fatty alcohols are also used as emollients. They are organic compounds that attach a hydroxyl group to a carbon that can be branched, saturated or unsaturated. Their chain length is greater than seven carbons. They are said to be less sticky and less heavy than many other fatty materials, such as the fatty acids. Examples of fatty alcohols which find use in the field of cosmetics and personal care products are cetyl alcohol, lauryl alcohol, stearyl alcohol and oleyl alcohol.

Fatty acid emollients are monocarboxylic acids with a chain length that is bigger than seven carbons. Some examples are typically compounds including lauric, myristic, palmitic, stearic, oleic, isostearic, ricinoleic, and behenic acid.

Ether emollients are compounds that contain oxygen atoms that are connected to two aryl or alkyl groups. Examples include ethoxyethane, methoxyethane, and phenoxybenzene.

Silicones emollients have silicone/oxygen monomers and are non-volatile. They include silicone compounds such as phenyltrimethicone, dimethicone a viscosity of more than about 5 cSt and dimethicone copolyol.

Hydrocarbon emollients are compounds carrying only carbon and hydrogen groups. These include aliphatic, cyclic, and aromatic groups. The main types used include mineral oil, Petrolatum, Squalane, Isododecane, Isohexadecane, Microcrystalline wax, Polyethylene, Ozokerite, and Paraffin wax.

A preferred emollient is isononyl isononanoate. Other suitable emollients include isopropyl palmitate, isopropyl myristate, triethyl citrate, PPG-20 Methyl Glucose Ether and/or caprylic/capric triglycerides.

The viscosity range of the fragrant product in this invention is 1 about to 200,000 cps.

Example 1

The table 1 lists the ingredients and composition of a viscous gel of the present invention. The gel is clear, sparkly and has a viscosity around 85,000 cps.

TABLE 1

| INGREDIENTS | PREFERRED WEIGHT % | RANGE IN WEIGHT % |
|---|---|---|
| BeauSil Gel 8065 (dimethicone/dimethicone crosspolymer gel) | 64.80 | 50-75 |
| DROM "Eternal Bliss" (fragrance oil) | 17.45 | 0.01-30 |
| ICM SF-1.5 (Decamethyltetrasiloxane) | 17.35 | 5-40 |
| Isononyl isononanoate | 0 | 0-30 |
| BHT (butylated hydroxytoluene) | 0.1 | 0-0.5 |
| Pigments (e.g. Glamour CF Hot Pink) (Aluminum Calcium Sodium Silicate and Titanium Dioxide and Tin Oxide and Red 7 Lake) | 0.3 | 0-5 |

Example 2

The table 2 lists the ingredients and composition of a clear Fragrant gel.

TABLE 2

| INGREDIENTS | PREFERRED WEIGHT % | RANGE IN WEIGHT % |
|---|---|---|
| BeauSil Gel 8065 (dimethicone/dimethicone crosspolymer gel) | 50.0 | 50-75 |
| DROM "Eternal Bliss" (fragrance oil) | 17.5 | 0.01-30 |
| ICM SF-1.5 (Decamethyltetrasiloxane) | 32.4 | 5-40 |
| Isononyl isononanoate | 0 | 0-30 |
| BHT (butylated hydroxytoluene) | 0.1 | 0-0.5 |
| Pigments | 0 | 0-5 |

Example 3

The table 3 lists the ingredients and composition of a clear Fragrant gel with a low level of fragrance.

TABLE 3

| INGREDIENTS | PREFERRED WEIGHT % | RANGE IN WEIGHT % |
|---|---|---|
| BeauSil Gel 8065 (dimethicone/dimethicone crosspolymer gel) | 60.0 | 50-75 |
| DROM "Eternal Bliss" (fragrance oil) | 0.5 | 0.01-30 |
| ICM SF-1.5 (Decamethyltetrasiloxane) | 39.4 | 5-40 |
| Isononyl isononanoate | 0 | 0-30 |
| BHT (butylated hydroxytoluene) | 0.1 | 0-0.5 |
| Pigments | 0 | 0-5 |

The invention claimed is:
1. An anhydrous alcohol-free and slow fragrance diffusive composition consisting of:
   50 to 75 percent by weight an anhydrous dimethicone crosspolymer gel, consisting of:
   7-20% dimethicone crosspolymer in linear silicone fluid;
   0.01 to 30 percent by weight a non-polar fragrance oil;
   5 to 40 percent by weight a volatile linear silicone fluid with a low average molecular weight and a relatively low viscosity between 0.6 and 3.0 cSt, wherein the volatile linear silicone fluid is represented by the formula:

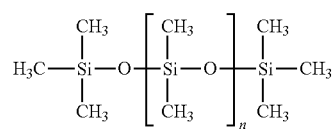

an emollient that is a linear or branched ester with a carbon chain of up to 10 carbon atoms;
optionally a preservative; and
optionally one or more pigments,
wherein a viscosity of the composition is adjusted based on a ratio of the volatile linear silicone fluid and the dimethicone crosspolymer gel, wherein the composition manifests an extended release of fragrance notes with moisturizing, miscibility, clarity, and original fragrance rendition.

2. The composition of claim 1, wherein the volatile linear silicone fluid is dimethicone.

3. The composition of claim 1, wherein the emollient is one or more of: isononyl isononanoate, triethyl citrate, isooctyl isooctanoate, diisopropyl adipate, glycerin heptanoate, ethylhexyl caprylate, diisopropyl sebacate, neopentylglycol diheptanoate, and isodecyl neopentanoate; and/or combinations thereof.

4. The composition of claim 1, wherein the emollient is one or more of PPG-20 Methyl Glucose Ether, caprylic/capric triglycerides and/or combinations thereof.

5. The composition of claim 1, wherein the emollient is one or more of: fatty alcohols, fatty acids, ethers, silicones and hydrocarbons.

6. The composition of claim 1, wherein the emollient is represented by the formula $R_i$—COO—R, R and $R_i$, wherein $R_i$ and R includes same or different carbon chain lengths.

7. The composition of claim 1, wherein the emollient is triethyl citrate.

8. The composition of claim 1, wherein the emollient is PPG-20 Methyl Glucose Ether.

9. The composition of claim 1, wherein the emollient is caprylic/capric triglycerides.

10. The composition of claim 1, wherein the dimethicone crosspolymer gel consisting of 8-12% dimethicone crosspolymer in linear silicone fluid.

11. The composition of claim 1, wherein the volatile linear silicone fluid is represented by the formula

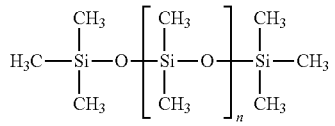

wherein n is an integer between 0 and 6.

12. The composition of claim 1, wherein n is an integer between 1 and 4.

13. The composition of claim 1, wherein the volatile silicone fluid is a pure silicone polymer.

* * * * *